US00PP36641P2

(12) United States Plant Patent
Meilland

(10) Patent No.: US PP36,641 P2
(45) Date of Patent: May 6, 2025

(54) BEDDING ROSE PLANT NAMED 'MEIWENTAR'

(50) Latin Name: *Rosa hybrida*
Varietal Denomination: MEIWENTAR

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/978,805

(22) Filed: Dec. 12, 2024

(51) Int. Cl.
*A01H 5/02* (2018.01)
*A01H 6/74* (2018.01)

(52) U.S. Cl.
USPC ..... Plt./101
CPC ..... *A01H 6/749* (2018.05)

(58) Field of Classification Search
USPC ..... Plt./101
CPC ..... A01H 6/749; A01H 5/02
See application file for complete search history.

(56) References Cited

U.S. PATENT DOCUMENTS

PP31,645 P2 4/2020 Sproul

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of bedding rose plant, referred to by its cultivar name, 'MEIWENTAR', is described. The new variety exhibits a compact growth habit. The flowers form a striped coloration. Ornamental dense semi-glossy foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'MEIWENTAR'.

STATEMENT REGARDING PRIOR DISCLOSURES BY THE INVENTOR

The first sale of the new variety was Feb. 1, 2024, in the United States of America from STAR® Roses and Plants. The first offer for sale and first sale of the new variety, and subsequent offer for sales and sales, was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding in Le Cannet de Maures, Var, France by artificial pollination wherein two parents were crossed which previously had been studied in the hope that they would contribute the desired characteristics. The female parent (i.e., the seed parent) of the new variety was the 'MEIGELSI' variety (not patented). The male parent (i.e., the pollen parent) of the new variety was an unnamed seeding (not patented) which was the product of the cross between the 'KORFALT' variety (not patented) and an unnamed seedling (not patented).

The parentage of the new variety can be summarized as follows:

'MEIGELSI' x ('KORFALT' x unnamed seedling)

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, and hardwood cuttings. Asexual propagation by the above-mentioned techniques in Le Cannet des Maures, Var, France has shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of bedding rose plant of the present invention possesses the following combination of characteristics:

(a) exhibits a compact growth habit,
(b) displays a striped flower coloration, and
(c) forms dense semi-glossy foliage.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the 'MEIGELSI' variety (i.e., the seed parent) displays flowers that are not striped colored compared to the flowers of the new variety that display petals with striped coloration. Additionally, the new variety exhibits a double flower form, whereas the unnamed seedling male parent ('KORFALT' x unnamed seedling) (i.e., the pollen parent) exhibits a semi-double flower form. Moreover, the new variety can be readily distinguished from non-parental related similar varieties. For example, the 'Sproulsun' variety (U.S. Plant Pat. No. 31,645) displays striped blossoms with a darker pink color compared to the striped blossoms of the new variety.

The new variety has been named the 'MEIWENTAR' variety.

BRIEF DESCRIPTION OF THE PHOTOGRAPHS

The accompanying photograph shows, as nearly true as it is reasonably possible to make the same in a color illustration of this character, typical specimens of the plant parts of the new variety. The rose plants of the new variety were approximately nine years of age and were observed during September while budded on their own roots and growing outdoors at Le Cannet des Maures, Var, France. Dimensions in centimeters are indicated at the bottom of the photograph.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the pistils (stamens removed).

Element 11—illustrates a specimen of a floral receptacle showing arrangement of the stamens and pistils.

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms. The R.H.S. Colour Chart designation used herein represents the closest color observed on the majority of the specified botanical feature. The description is based on a nine-year-old specimen of the new variety, observed during September, while budded on its own roots and growing outdoors at Le Cannet des Maures, Var, France.

Botanical classification: *Rosa hybrida* cultivar 'MEIWENTAR'.

Commercial classification: Bedding Rose Plant.

Plant:

*Habit*.—Bushy.

*Height*.—Approximately 45.0 cm on average.

*Width*.—Approximately 60.0 cm on average.

Branches:

*Stem color*.—Young stems: Yellow-Green Group 144A. — adult wood: Green Group 137C.

Length.—From the crown to the flower is typically between 10.0cm to 35.0 cm.

*Diameter*.—Typically between 0.2 cm to 0.5 cm.

*Prickles*.—Configuration on adult stems: sinusoidal, elongated, and curved downwards on the upper surface and concave on the under surface. — long prickles — quantity: approximately 10 thorns on average per 10 cm long young stem and approximately 10 thorns on average per 10 cm long adult stem. — long prickles — length: typically between 0.4 cm to 0.5 cm on young stems and on adult stems. — long prickles — width at base: typically between 0.2 cm to 0.5 cm on young stems and on adult stems. — long prickles — base shape: obovate, narrow, and medium on young stems and on adult stems. — long prickles — color on young stems: Yellow-Green Group 145B more or less suffused with anthocyanin coloration of Greyed-Purple Group 186B. — long prickles — color on adult stems: Greyed-Orange Group 165A. — small prickles — quantity: none observed on young stems and approximately 15 thorns on average per 10 cm long adult stem. — small prickles — length: approximately 0.1 cm on average on adult stems. — small prickles — width at base: typically less than 0.1 cm on average on adult stems. — small prickles — base shape: obovate, narrow, and short on adult stems. — small prickles — color on adult stems: Greyed-Orange Group 165A

*Anthocyanin coloration of young shoots*.—Greyed-Purple Group 178A.

*Internode numbers on entire branch*.—Typically between 5 to 7.

*Internode length*.—Typically between 2.5 cm to 7.0 cm.

Leaflets:

*Number*.—3, 7, and most often 5.

*Shape*.—Tip: acuminate to attenuate. base: obtuse.

*Serration*.—Small and single.

*General appearance*.—Lanceolate.

*Undulation*.—Weak.

*Glossiness of upper side*.—Medium.

*Texture*.—Moderately leathery.

*Smoothness*.—Upper surface: bumpy. — under surface: rough.

*Venation*.—Color is Yellow-Green Group 146D; and pattern is imparipinnate.

*Size*.—Terminal leaflet: length is typically between 3.5 cm to 6.0 cm; width is typically between 2.8 cm to 3.8 cm. — 5-leaflet leaf: length is typically between 10.5 cm to 12.0 cm; width is typically between 6.0 cm to 9.0 cm.

Foliage:

*General appearance*.—Rather dense with a semi-glossy aspect.

*New foliage*.—Upper surface color: Green Group 137A more or less suffused with anthocyanin coloration of Greyed- Purple Group 183A. — under surface color: Green Group 138B amply suffused with anthocyanin coloration near Greyed-Purple Group 183D.

*Adult foliage*.—Upper surface color: Green Group 137A. — under surface color: Green Group 138B.

*Petiole*.—Texture: upper surface is smooth and glandular; under smooth with a few prickles. — length: typically between 2.2 cm to 3.0 cm. — width: approximately 0.1 cm on average. — upper surface color: Green Group 137A. — under surface color: Yellow-Green Group 144A.

*Rachis*.—Rachis length of terminal leaflet: typically between 3.0 cm to 5.0 cm. — rachis width of terminal leaflet: approximately 0.1 cm on average. — texture: upper surface is smooth; under surface is a few prickles. — upper surface color: Green Group 137A. — under surface color: Yellow-Green Group 144A.

*Stipules*.—Length: approximately 1.5 cm on average. — width: approximately 0.1 cm on average. — general appearance: narrow. — texture: upper and under surfaces are smooth. — upper surface color: Green Group 137A. — under surface color: Green Group 138A.

Inflorescence:

*Number of flowers per stem*.—Typically between 1 to 5 flowers per stem.

*Lastingness of the bloom*.—On the plant: approximately 7 days on average. — in vase: not tested.

*Bud*.—Shape: ovoid. — size: small to medium — length: approximately 2.0 cm on average. — width: approximately 1.3 cm on average. — color as calyx breaks: upper surface: a color in between Red Group 46A and Red Group 53A and slightly striped with Greyed-Yellow Group 161C; basal spot is Yellow Group 3B. under surface: Red Group 46A; basal spot is Yellow Group 3A.

*Sepals*.—Number: commonly 5 (sometimes 6). — length: typically between 1.8 cm to 2.5 cm. — width: typically between 0.6 cm to 0.8 cm. — shape: at the top: elongated and narrow. at the base: flat at union with the receptacle. — extensions: typically 2 to 3 sepals with 1 or 7 extensions with a length typically between 0.1 cm and 0.5 cm and a width typically between 0.5 mm to 2.0 mm. — upper surface: texture: tomentous. color: Green Group 138B. — under surface: texture: smooth. color: a color in between Green Group 143A and Yellow-Green Group 144A.

*Receptacle*.—Color: Green Group 143B. — length: typically between 0.7 cm to 1.0 cm. — width: typically between 0.8 cm to 1.1 cm. — surface: smooth. — shape: pitcher shaped.

*Peduncle*.—Length: typically between 5.0 cm to 5.5 cm. — width: approximately 0.2 cm on average. — surface: little prickles. — color: Yellow-Green Group 144A.

*Flower*.—Diameter when open: typically between 5.0 cm to 7.0 cm. — depth of the flower: typically between 2.0 cm to 3.0 cm. — shape: flat cup shaped. — shape when viewed from above: irregularly rounded. — shape of the upper part of the flower profile: flat. — shape of the lower part of the flower profile: flat, slightly rounded. — type: double. — number of petals under normal conditions: approximately 90 on average. — petals: shape: obovate (truncated at the top and cuneiform at the base). texture: flexible. length: typically between 1.8 cm to 2.8 cm. width: typically between 1.0 cm to 2.8 cm. — undulation of the petal: very weak. — reflexing of the petal: medium. — petal incision: very weak. — petal arrangement: imbricated with rare petaloid-like deformed petals. — petal drop: petals drop off cleanly before drying. — fragrance: very slight. — discoloration of the flower at end of bloom: upper surface is Red-Purple Group 73A and under surface is Purple Group 75D. — color when opening: basal spot on the upper surface: Yellow Group 7A. upper surface: Red Group 53C striped with Yellow Group 3D. basal spot on the under surface: Yellow Group 7A. under surface: Red Group 46D striped with Yellow Group 3D. — color of the open flower: basal spot on upper surface: Yellow Group 7A. upper surface: Red-Purple Group 57A striped with Yellow Group 3D evolving to Yellow-White Group 158D. basal spot on under surface: Yellow Group 3D. under surface of the flower: Yellow-White Group 158D amply suffused and striped with Red-Purple Group 57A. — anthers: approximately 180 on average, length is approximately 0.2 cm on average, width is approximately 0.1 cm on average, coloration is Greyed-Orange Group 163B, and arrangement is regular around styles. — filaments: length is typically between 0.1 cm and 0.5 cm, and coloration is Yellow-Orange Group 14A. — styles: length is typically between 0.4 cm to 0.6 cm, coloration is Green-White Group 157B, and number is approximately 180 on average. — stigmas: length is typically less than 0.1 cm and coloration is Yellow-Orange Group 14B. — pollen: medium quantity; color is Greyed-Yellow Group 160B. — hips: none observed.

Development:

*Vegetation*.—Medium.

*Blossoming*.—Early in the season, abundant and intermittent (typically from May to October in France).

*Resistance to diseases*.—Good resistance for rust (*Phragmidium* sp.).

*Hardiness*.—Tested up to USDA Zone 5 to Zone 9.

The new 'MEIWENTAR' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of bedding rose plant named 'MEIWENTAR' characterized by the following combination of characteristics:

(a) exhibits a compact growth habit, (b) displays a striped flower coloration, and (c) forms dense semi-glossy foliage;

substantially as herein shown and described.

* * * * *

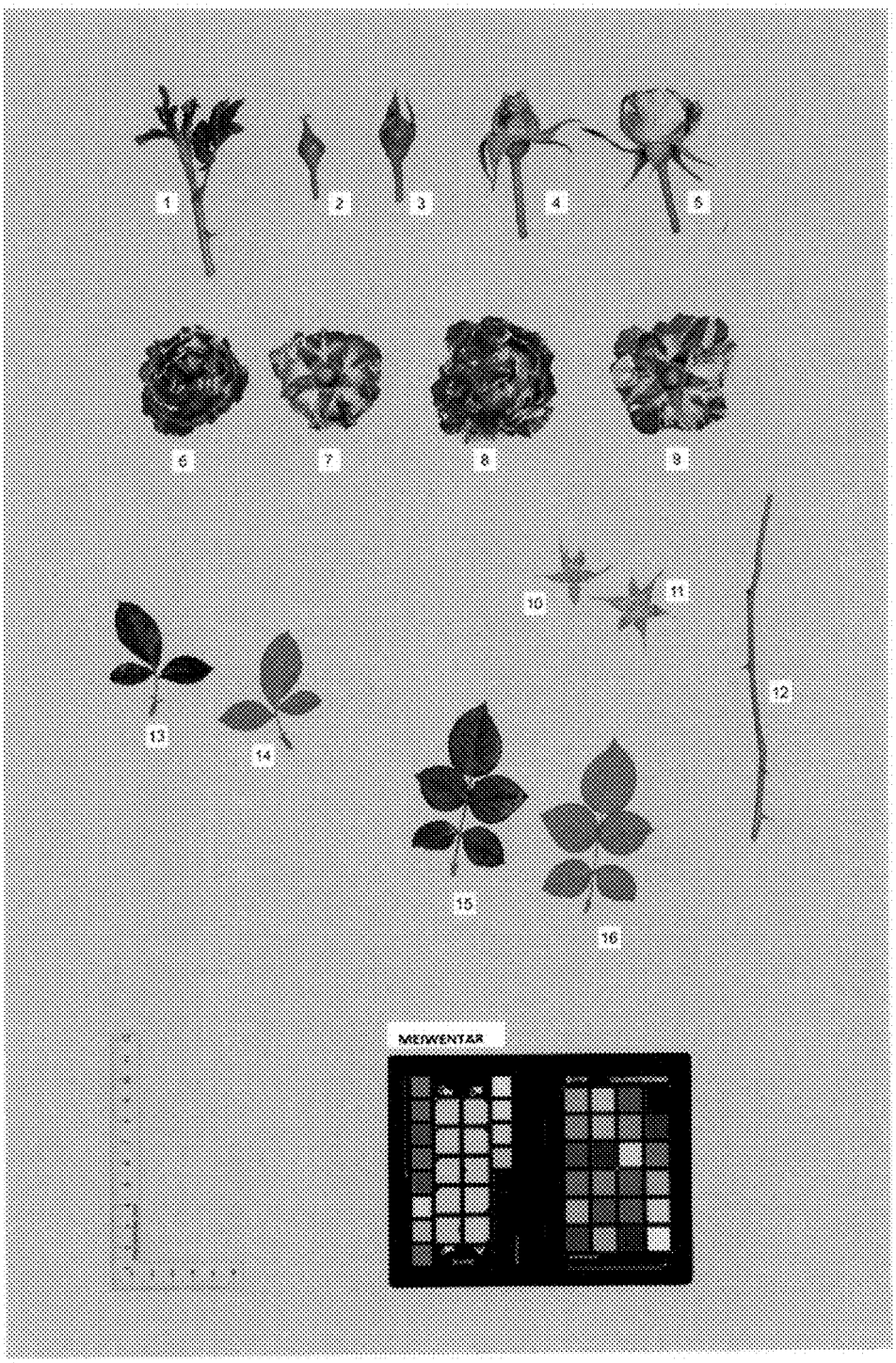
1
2
3
4
5
6
7
8
9
10
11
12
13
14
15
16
MEWENTAR